(12) United States Patent
Smith et al.

(10) Patent No.: US 10,463,427 B2
(45) Date of Patent: Nov. 5, 2019

(54) SELECTIVE STIFFENING CATHETER

(71) Applicant: Syntheon, LLC, Miami, FL (US)

(72) Inventors: Kevin W. Smith, Coral Gables, FL (US); Matthew A. Palmer, Miami, FL (US); M. Sean McBrayer, Coral Gables, FL (US); Thomas O. Bales, Jr., Miami, FL (US); Derek Dee Deville, Coral Gables, FL (US); Joe Abelleira, New Port Richey, FL (US)

(73) Assignee: Syn Variflex, LLC, Miami, FL (US)

( * ) Notice: Subject to any disclaimer, the term of this patent is extended or adjusted under 35 U.S.C. 154(b) by 0 days.

(21) Appl. No.: 15/891,150

(22) Filed: Feb. 7, 2018

(65) Prior Publication Data

US 2018/0193091 A1    Jul. 12, 2018

Related U.S. Application Data

(63) Continuation of application No. 15/054,983, filed on Feb. 26, 2016, now Pat. No. 10,159,527, which is a
(Continued)

(51) Int. Cl.
*A61M 25/00* (2006.01)
*A61B 18/14* (2006.01)
(Continued)

(52) U.S. Cl.
CPC .......... *A61B 18/1492* (2013.01); *A61B 18/00* (2013.01); *A61F 2/01* (2013.01);
(Continued)

(58) Field of Classification Search
CPC ............... A61B 18/1492; A61B 18/00; A61B 2018/00351; A61B 2018/00577;
(Continued)

(56) References Cited

U.S. PATENT DOCUMENTS 3,359,974 A    12/1967    Khalil
3,557,780 A    1/1971    Sato
(Continued)

FOREIGN PATENT DOCUMENTS

| WO | 2005048814 A2 | 6/2005 |
| WO | 2007093394 A1 | 8/2007 |
| WO | 2007131766 A2 | 11/2007 |

OTHER PUBLICATIONS

International Search Report and Written Opinion of the International Searching Authority dated Aug. 31, 2006, for International Application No. PCT/US2005/034487.
(Continued)

*Primary Examiner* — Amber R Stiles
(74) *Attorney, Agent, or Firm* — Gregory L. Mayback; Dickinson Wright PLLC

(57) ABSTRACT

A controllable stiffness catheter comprising a shaft comprising an inner sheath defining an access lumen, an outer sheath surrounding the inner sheath and defining an annulus therebetween, the annulus having a vacuum connection at which a vacuum is applied to the annulus, and a mechanical stiffener disposed at least at a portion of the annulus.

20 Claims, 9 Drawing Sheets

Related U.S. Application Data continuation of application No. 13/919,080, filed on Jun. 17, 2013, now Pat. No. 9,295,511, which is a continuation of application No. 12/822,219, filed on Jun. 24, 2010, now Pat. No. 8,491,520, which is a continuation of application No. 11/395,903, filed on Mar. 31, 2006, now Pat. No. 7,771,411, which is a continuation-in-part of application No. 11/233,993, filed on Sep. 23, 2005, now Pat. No. 7,559,916.

(60) Provisional application No. 60/612,684, filed on Sep. 24, 2004.

(51) Int. Cl.
  *A61F 2/01* (2006.01)
  *A61M 25/01* (2006.01)
  *A61B 18/00* (2006.01)
  *A61M 25/10* (2013.01)

(52) U.S. Cl.
  CPC ...... *A61M 25/005* (2013.01); *A61M 25/0054* (2013.01); *A61M 25/01* (2013.01); *A61B 2018/00351* (2013.01); *A61B 2018/00357* (2013.01); *A61B 2018/00577* (2013.01); *A61F 2230/005* (2013.01); *A61M 25/0053* (2013.01); *A61M 25/104* (2013.01); *A61M 2025/0063* (2013.01); *A61M 2025/0064* (2013.01)

(58) Field of Classification Search
  CPC ...... A61B 2018/00357; A61M 25/005; A61M 25/0054; A61M 25/01; A61M 25/104; A61M 2025/0064; A61M 2025/0063; A61M 25/0053; A61F 2/01; A61F 2230/005
  See application file for complete search history.

(56) References Cited

U.S. PATENT DOCUMENTS

| | | | |
|---|---|---|---|
| 3,998,216 A | 12/1976 | Hosono | |
| 4,176,662 A | 12/1979 | Frazer | |
| 4,248,234 A | 2/1981 | Assenza et al. | |
| 4,498,473 A | 2/1985 | Gereg | |
| 4,571,240 A | 2/1986 | Samson et al. | |
| 4,575,185 A | 3/1986 | Wentzell | |
| 4,581,390 A | 4/1986 | Flynn | |
| 4,753,223 A | 6/1988 | Bremer | |
| 4,762,118 A | 8/1988 | Lia et al. | |
| 4,784,636 A | 11/1988 | Rydell | |
| 4,815,450 A | 3/1989 | Patel | |
| 4,817,613 A | 4/1989 | Jaraczewski et al. | |
| 4,838,859 A | 6/1989 | Strassmann | |
| 4,848,364 A * | 7/1989 | Bosman ............... A61F 2/0063 128/849 |
| 4,890,602 A | 1/1990 | Hake | |
| 4,893,613 A | 1/1990 | Hake | |
| 4,909,787 A | 3/1990 | Danforth | |
| 4,984,581 A | 1/1991 | Stice | |
| 4,998,282 A | 3/1991 | Shishido et al. | |
| 5,069,674 A | 12/1991 | Fearnot et al. | |
| 5,143,085 A | 9/1992 | Wilson | |
| 5,211,633 A | 5/1993 | Stouder, Jr. | |
| 5,222,938 A | 6/1993 | Behl | |
| D337,733 S | 7/1993 | Ewing et al. | |
| 5,240,135 A * | 8/1993 | Lepinoy ............... A61F 5/05833 206/522 |
| 5,259,366 A | 11/1993 | Reydel et al. | |
| 5,271,382 A | 12/1993 | Chikama | |
| 5,337,733 A | 8/1994 | Bauerfeind et al. | |
| 5,357,979 A | 10/1994 | Imran | |
| 5,386,817 A | 2/1995 | Jones | |
| 5,423,771 A | 6/1995 | Imran | |
| 5,454,795 A | 10/1995 | Samson | |
| 5,531,685 A | 7/1996 | Hemmer et al. | |
| 5,577,992 A | 11/1996 | Chiba et al. | |
| 5,649,941 A * | 7/1997 | Lary ............... A61B 17/3207 604/22 |
| 5,738,100 A | 4/1998 | Yagami et al. | |
| 5,759,151 A | 6/1998 | Sturges | |
| 5,807,237 A | 9/1998 | Tindel | |
| 5,851,203 A * | 12/1998 | van Muiden ..... A61M 25/0054 604/525 |
| 5,873,816 A | 2/1999 | Kagawa et al. | |
| 5,897,536 A | 4/1999 | Nap et al. | |
| 5,931,819 A | 8/1999 | Fariabi | |
| 5,938,623 A | 8/1999 | Quiachon et al. | |
| 6,024,740 A | 2/2000 | Lesh et al. | |
| 6,030,405 A | 2/2000 | Zarbatany et al. | |
| 6,117,068 A | 9/2000 | Gourley et al. | |
| 6,123,084 A | 9/2000 | Jandak et al. | |
| 6,146,339 A | 11/2000 | Biagtan et al. | |
| 6,159,187 A | 12/2000 | Park et al. | |
| 6,196,967 B1 | 3/2001 | Lim et al. | |
| 6,217,565 B1 | 4/2001 | Cohen | |
| 6,309,412 B1 | 10/2001 | Lau et al. | |
| 6,346,077 B1 | 2/2002 | Taylor et al. | |
| 6,375,654 B1 | 4/2002 | McIntyre | |
| 6,387,044 B1 | 5/2002 | Tachibana et al. | |
| 6,451,005 B1 | 9/2002 | Saitou et al. | |
| 6,468,203 B2 | 10/2002 | Belson | |
| 6,478,731 B2 | 11/2002 | Speier et al. | |
| 6,506,150 B1 | 1/2003 | Ouchi | |
| 6,517,477 B1 | 2/2003 | Wendlandt | |
| 6,533,752 B1 | 3/2003 | Waram et al. | |
| 6,562,021 B1 | 5/2003 | Derbin et al. | |
| 6,602,242 B1 | 8/2003 | Fung et al. | |
| 6,610,007 B2 | 8/2003 | Belson et al. | |
| 6,645,223 B2 | 11/2003 | Boyle et al. | |
| 6,800,056 B2 | 10/2004 | Tartaglia et al. | |
| 6,802,809 B2 | 10/2004 | Okada | |
| 6,858,005 B2 | 2/2005 | Online et al. | |
| 6,887,235 B2 | 5/2005 | O'Connor et al. | |
| 6,926,669 B1 | 8/2005 | Stewart | |
| 6,942,613 B2 | 9/2005 | Ewers et al. | |
| 6,974,411 B2 | 12/2005 | Belson | |
| 6,984,203 B2 | 1/2006 | Tartaglia et al. | |
| 7,066,880 B2 | 6/2006 | Wendlandt | |
| 7,066,931 B2 | 6/2006 | O'Connor et al. | |
| 7,104,951 B2 | 9/2006 | Hasegawa et al. | |
| 7,291,127 B2 | 11/2007 | Eidenschink | |
| 7,435,214 B2 | 10/2008 | Kucklick et al. | |
| 7,771,411 B2 | 8/2010 | Smith et al. | |
| 7,811,228 B2 | 10/2010 | Adams | |
| 8,092,374 B2 | 1/2012 | Smith et al. | |
| 8,308,722 B2 | 11/2012 | Ormsby et al. | |
| 8,491,520 B2 | 7/2013 | Smith et al. | |
| 8,556,804 B2 | 10/2013 | Smith et al. | |
| 9,155,451 B2 | 10/2015 | Smith et al. | |
| 2002/0002323 A1 | 1/2002 | Moriyama | |
| 2002/0082585 A1 | 6/2002 | Carroll et al. | |
| 2002/0177750 A1 | 11/2002 | Pilvisto | |
| 2003/0125764 A1* | 7/2003 | Brady ............... A61F 2/01 606/200 |
| 2003/0135198 A1 | 7/2003 | Berhow et al. | |
| 2004/0034383 A1* | 2/2004 | Belson ............... A61M 25/0054 606/191 |
| 2004/0044350 A1 | 3/2004 | Martin et al. | |
| 2004/0054322 A1* | 3/2004 | Vargas ............... A61M 25/00 604/95.04 |
| 2004/0138529 A1 | 7/2004 | Wiltshire et al. | |
| 2004/0182393 A1 | 9/2004 | MacMillan et al. | |
| 2004/0186350 A1 | 9/2004 | Brenneman et al. | |
| 2005/0075538 A1 | 4/2005 | Banik et al. | |
| 2005/0131279 A1 | 6/2005 | Boulais et al. | |
| 2005/0165275 A1 | 7/2005 | Von Felten et al. | |
| 2006/0025652 A1 | 2/2006 | Vargas | |
| 2006/0069346 A1 | 3/2006 | Smith et al. | |
| 2006/0129130 A1 | 6/2006 | Tal et al. | |
| 2006/0211979 A1 | 9/2006 | Smith et al. | |
| 2007/0088367 A1 | 4/2007 | Von Weymarn-Scharli | |
| 2007/0093689 A1 | 4/2007 | Steinberg | |

(56) References Cited

U.S. PATENT DOCUMENTS

| | | |
|---|---|---|
| 2007/0179339 A1 | 8/2007 | Gorini et al. |
| 2007/0208300 A1 | 9/2007 | Pravong et al. |
| 2007/0215268 A1 | 9/2007 | Pingleton et al. |
| 2007/0270648 A1 | 11/2007 | Smith et al. |
| 2007/0272648 A1 | 11/2007 | Keiji et al. |
| 2008/0009831 A1 | 1/2008 | Griffin |
| 2008/0091170 A1 | 4/2008 | Vargas et al. |
| 2008/0269776 A1 | 10/2008 | Justin et al. |
| 2009/0149710 A1 | 6/2009 | Stefanchik et al. |
| 2015/0272654 A1 | 10/2015 | Esch et al. |
| 2016/0101261 A1 | 4/2016 | Kugler et al. |
| 2018/0199991 A1* | 7/2018 | Smith ............... A61B 18/1492 |

OTHER PUBLICATIONS

Yarmolenko, et al. NIH Public Access National Institutes of Health, "Thresholds for thermal damage to normal tissues: An update" Int J Hyperthermia. Author manuscript; available in PMC 2013 Mar. 27, 2011 informa UK Ltd.; 27(4): 320-343. doi:10.3109/02656736.2010.534527.

Cordaro, et al.,Thermodynamic Properties of Molten Nitrate Salts, Sandia National Laboratories: Senior member, Technical Staff, PHD. Livermore, CA, pp. 1-8.

Abstract submitted to A/S/G/E, C W Williams, "A Split Overtube for Easier Colonoscopy", Gastrointestial Endoscopt, 1983, p. 188.

International Search Report for PCT/US/068348 dated Oct. 30, 2008.

International Search Report for PCT/US07/05478 dated Dec. 17, 2007.

International Search Report for PCT/US07/12179 dated Sep. 12, 2008.

International Search Report for PCT/US07/75701 dated Aug. 29, 2008.

International Search Report for PCT/US08/64084 dated Dec. 9, 2008.

International Search Report an Written Opinion in PCT/US2018/026877 dated Jun. 11, 2018.

* cited by examiner

SELECTIVE STIFFENING CATHETER

CROSS-REFERENCE TO RELATED APPLICATION

This application is a continuation of U.S. patent application Ser. No. 15/054,983, filed Feb. 26, 2016, which application:
is a continuation of copending U.S. patent application Ser. No. 13/919,080, filed Jun. 17, 2013, now U.S. Pat. No. 9,295,511, issued on Mar. 29, 2016, which application:
is a continuation of U.S. patent application Ser. No. 12/822,219 filed on Jun. 24, 2010, now U.S. Pat. No. 8,491,520 issued on Jul. 23, 2013, which application:
is a continuation of U.S. patent application Ser. No. 11/395,903 filed on Mar. 31, 2006, now U.S. Pat. No. 7,771,411 issued on Aug. 10, 2010, which application:
is a continuation-in-part of U.S. patent application Ser. No. 11/233,993, filed Sep. 23, 2005, now U.S. Pat. No. 7,559,916 issued on Jul. 14, 2009 (which application claims the priority, under 35 U.S.C. § 119, of U.S. Provisional Patent Application No. 60/612,684, filed Sep. 24, 2004),
the entire disclosures of which are hereby incorporated herein by reference in their entireties.

STATEMENT REGARDING FEDERALLY SPONSORED RESEARCH OR DEVELOPMENT

Not Applicable

FIELD OF THE INVENTION

The invention lies in the field of medical devices, namely, catheters. In particular, the invention relates to catheters that can change stiffness characteristics in use and their uses.

BACKGROUND OF THE INVENTION

To gain access to treatment sites in the body, catheters must be flexible enough to conform to and follow natural anatomical pathways as they are advanced. These pathways can be quite tortuous, made of soft and delicate tissues with many twists and turns. In the vasculature, this is especially the case, and even more so in certain areas of the vasculature such as the vessels of the brain and the coronary arteries.

When treating a site in the vasculature, the state-of-the-art practice is to first gain access to the treatment site with a flexible, steerable guidewire. Such a guidewire can be precisely controlled by the physician and steered into place using radiographic guidance. Once the guidewire is in-place, the catheter is advanced over the guidewire. The catheter must be flexible enough to smoothly follow the pathway of guidewire. The catheter can, then, be used to deliver the treatment.

In the case of arterial blockage, the catheter may be a balloon dilatation catheter that is used to open the blockage. The guidewire is, first, passed beyond the lesion, and the catheter is advanced over the guidewire and through the lesion. In the case of complete or nearly complete blockage, the force required to advance the guidewire through the lesion can be difficult for the physician to generate by pushing on the flexible guidewire from the arterial access site. Further, this access site may be far from the treatment site, such as in the case of coronary arterial treatment where access to the coronary arteries is gained though the femoral artery. In such a situation, the physician is trying to advance the flexible guidewire through an obstruction over 100 cm away from where he/she is pushing. The same flexibility that helped gain access to the treatment site now inhibits the advancement of the guidewire. The guidewire bends and buckles under the strain and very little thrust is delivered to the tip of the guidewire.

Current practice advances the balloon catheter up to the treatment site to provide support to the guidewire as it is advanced through the lesion. This is an improvement, but the catheter is also very flexible and provides little if any additional support. Specialty support catheters, which offer more support than balloon catheters, are also used. These provide an improvement over balloon catheters but are also limited by how flexible they must be to reach the treatment site.

The above-mentioned problems are compounded in the case of a total arterial blockage or Chronic Total Occlusion (CTO). Accordingly, most CTOs go untreated. And, there is no catheter-based standard accepted practice for CTO treatment. Currently, treatment of CTOs by catheter interventionalists is performed by attempting to pass a guidewire across the CTO. Once the guidewire is across, a low profile balloon catheter can be advanced over the guidewire to dilate the lesion. Such a procedure is almost always followed by placement of a stent. Specialty guidewires are available to aid the physician in this effort but they, too, are limited in their utility by the constraints of flexibility and compliance. It is noted that attempting to cross CTOs is a tedious practice with current equipment and is met with limited success.

Atrial fibrillation is the most common heart arrhythmia in the world, affecting over 2.5 million people in the United States alone. In atrial fibrillation, the electrical signals in the atrial (upper) chambers of the heart are chaotic. In addition, the atrial electrical impulses that reach the ventricles (lower heart chambers) often arrive at irregular intervals.

Ablation of cardiac tissue, to create scar tissue that poses an interruption in the path of the errant electrical impulses in the heart tissue, is a commonly performed procedure to treat cardiac arrhythmias. Such ablation may range from the ablation of a small area of heart tissue to a series of ablations forming a strategic placement of incisions in both atria to stop the conduction and formation of errant impulses.

Ablation has been achieved or suggested using a variety of techniques, such as freezing through cryogenic probe, heating through RF energy, surgical cutting, and other techniques. As used here, "ablation" means the removal or destruction of the function of a body part, such as cardiac tissue, regardless of the apparatus or process used to carry out the ablation. Also, as used herein, "transmural" means through the wall or thickness, such as through the wall or thickness of a hollow organ or vessel.

Ablation of cardiac tissue may be carried out in an open surgical procedure, where the breastbone is divided and the surgeon has direct access to the heart, or through a minimally invasive route, such as between the ribs or through a catheter that is introduced through a vein and into the heart. Types of ablation for atrial fibrillation include Pulmonary vein isolation ablation (PVI Ablation or PVA), cryoablation (freezing), and atrioventricular (AV) node ablation with pacemakers.

Prior to any ablation, the heart typically is electronically mapped to locate the point or points of tissue that are causing the arrhythmia. With minimally invasive procedures such as through a catheter, the catheter is directed to the aberrant tissue, and an electrode or cryogenic probe is placed in contact with the endocardial tissue. RF energy is delivered from the electrode to the tissue to heat and ablate the tissue (or the tissue may be frozen by the cryogenic probe), thus eliminating the source of the arrhythmia.

Common problems encountered in this procedure are difficulty in precisely locating the aberrant tissue, and complications related to the ablation of the tissue. Locating the area of tissue causing the arrhythmia often involves several hours of electrically "mapping" the inner surface of the heart using a variety of mapping catheters, and once the aberrant tissue is located, it is often difficult to position the catheter and the associated electrode or probe so that it is in contact with the desired tissue.

The application of either RF energy or ultra-low temperature freezing to the inside of the heart chamber also carries several risks and difficulties. It is very difficult to determine how much of the catheter electrode or cryogenic probe surface is in contact with the tissue since catheter electrodes and probes are cylindrical and the heart tissue cannot be visualized clearly with existing fluoroscopic technology. Further, because of the cylindrical shape, some of the exposed electrode or probe area will almost always be in contact with blood circulating in the heart, giving rise to a risk of clot formation.

Clot formation is almost always associated with RF energy or cryogenic delivery inside the heart because it is difficult to prevent the blood from being exposed to the electrode or probe surface. Some of the RF current flows through the blood between the electrode and the heart tissue and this blood is coagulated, or frozen when a cryogenic probe is used, possibly resulting in clot formation. When RF energy is applied, the temperature of the electrode is typically monitored so as to not exceed a preset level, but temperatures necessary to achieve tissue ablation almost always result in blood coagulum forming on the electrode.

Overheating or overcooling of tissue is also a major complication, because the temperature monitoring only gives the temperature of the electrode or probe, which is, respectively, being cooled or warmed on the outside by blood flow. The actual temperature of the tissue being ablated by the electrode or probe is usually considerably higher or lower than the electrode or probe temperature, and this can result in overheating, or even charring, of the tissue in the case of an RF electrode, or freezing of too much tissue by a cryogenic probe. Overheated or charred tissue can act as a locus for thrombus and clot formation, and over freezing can destroy more tissue than necessary. It is also very difficult to achieve ablation of tissue deep within the heart wall.

Other forms of energy have been used in ablation procedures, including ultrasound, cryogenic ablation, and microwave technology. When used from an endocardial approach, the limitations of all energy-based ablation technologies to date are the difficulty in achieving continuous transmural lesions and minimizing unnecessary damage to endocardial tissue. Ultrasonic and RF energy endocardial balloon technology has been developed to create circumferential lesions around the individual pulmonary veins. See e.g., U.S. Pat. No. 6,024,740 to Lesh et al. and U.S. Pat. Nos. 5,938,660 and 5,814,028 to Swartz et al. However, this technology creates rather wide (greater than 5 mm) lesions that could lead to stenosis (narrowing) of the pulmonary veins. The large lesion area can also act as a locus point for thrombus formation. Additionally, there is no feedback to determine when full transmural ablation has been achieved. Cryogenic ablation has been attempted both endocardially and epicardially (see e.g., U.S. Pat. No. 5,733,280 to Avitall, U.S. Pat. No. 5,147,355 to Friedman et al., and U.S. Pat. No. 5,423,807 to Milder, and WO 98/17187, the latter disclosing an angled cryogenic probe, one arm of which is inserted into the interior of the heart through an opening in the heart wall that is hemostatically sealed around the arm by a suture or staples), but because of the time required to freeze tissue, and the delivery systems used, it is difficult to create a continuous line, and uniform transmurality is difficult to verify.

International Publications WO99/56644 and WO99/56648 disclose an endocardial ablation catheter with a reference plate located on the epicardium to act as an indifferent electrode or backplate that is maintained at the reference level of the generator. Current flows either between the electrodes located on the catheter, or between the electrodes and the reference plate. It is important to note that this reference plate is essentially a monopolar reference pad. Consequently, there is no energy delivered at the backplate/tissue interface intended to ablate tissue. Instead, the energy is delivered at the electrode/tissue interface within the endocardium, and travels through the heart tissue either to another endocardial electrode, or to the backplate. Tissue ablation proceeds from the electrodes in contact with the endocardium outward to the epicardium. Other references disclose epicardial multi-electrode devices that deliver either monopolar or bipolar energy to the outside surface of the heart.

It is important to note that all endocardial ablation devices that attempt to ablate tissue through the full thickness of the cardiac wall have a risk associated with damaging structures within or on the outer surface of the cardiac wall. As an example, if a catheter is delivering energy from the inside of the atrium to the outside, and a coronary artery, the esophagus, or other critical structure is in contact with the atrial wall, the structure can be damaged by the transfer of energy from within the heart to the structure. The coronary arteries, esophagus, aorta, pulmonary veins, and pulmonary artery are all structures that are in contact with the outer wall of the atrium, and could be damaged by energy transmitted through the atrial wall.

Therefore, it would be beneficial to provide a catheter that can advance up to the treatment site with sufficient flexibility through a tortuous path and that can provide sufficient support to advance through a CTO lesion.

SUMMARY OF THE INVENTION

A catheter with controllable stiffness and a method for operating a selective stiffening catheter overcome the hereinafore-mentioned disadvantages of the heretofore-known devices and methods of this general type and can traverse a natural passage of the body in a first flexible state and can be made to change to a second stiffer state and cycle back and forth repeatedly between these states at will and that can traverse tortuous anatomy by conforming to it and, once in-place, can be made to stiffen and maintain its tortuous shape in the anatomy.

The catheter provides a platform on which physicians can deliver tools to treatment sites to aid in the crossing of arterial blockages, especially, CTOs. In the stiff state, these tools can be used and the force applied by the tools on the treatment site can be enhanced and increased based upon the stiffness properties of the catheter.

The catheter according to the invention has a stiffness that can be controlled during use. The stiffness of the catheter can be changed during use from soft and flexible to firm and stiff, and back again, if desired. The entire length of the catheter can be made to change its stiffness characteristics. Alternatively, and/or additionally, any portion or portions of the device can be configured to change its stiffness characteristics as well.

The catheter is delivered to the treatment site in the flexible state, in which, it will track over the guidewire and conform to the anatomical pathway, e.g., the vasculature. Once in-place, the catheter can be made to become stiff (either in whole or in part) without straightening and, thereby, maintain its conformance to the vasculature. In such a state, the catheter provides a stiff conduit to deliver tools to the treatment site without compromising the natural anatomy. This stiffness provides the support necessary to efficiently advance the guide or crossing wires without loss of motion and efficiently transmit thrust loads to the tools.

In the case of a guidewire as described above, the guidewire will, with use of the catheter according to the invention, not flex away from the treatment site when pushed and provides great increases in feel, control, and thrust. Such characteristics aid in the successful crossing of difficult-to-cross lesions and provide an opportunity to cross CTOs.

The vasculature example above has been used to describe the problem and embodiments of the present invention, but it can be appreciated that this same concept can be used in any part of the body.

With the foregoing and other objects in view, there is provided, in accordance with the invention, a method for delivering radiofrequency (RF) energy to living tissue. A guidewire is extended to a tissue treatment site in a body. A controllable stiffness catheter is provided and has a shaft having a distal end, a stiffness sheath, and an access lumen, a stiffness device disposed at the stiffness sheath, having non-metallic properties, and being in a relatively stiff state at or below a first temperature and being in a relatively soft state at or above a second temperature, the relatively soft state being entered in response to a change in the non-metallic properties of the stiffness device, a temperature-changing device in thermal contact with the stiffness device, the temperature-changing device changing a temperature of the stiffness device at least below the first temperature and above the second temperature, a power controller electrically connected to the stiffness device and selectively supplying power to the temperature-changing device to change a stiffness of the stiffness device between the stiff state and the soft state, and an RF energy supply device having at least a portion thereof disposed at the distal end of the shaft for selectively supplying RF energy from the distal end. While supplying power to the temperature-changing device, the controllable stiffness catheter is threaded along the guidewire up to the treatment site. Power is removed from the temperature-changing device to alter the non-metallic properties of the stiffness device and directly result in a change of stiffness of the stiffness device to the stiff state without straightening the catheter. The RF energy supply device physically contacts the treatment site and RF energy is delivered to the treatment site from the RF energy supply device.

In accordance with another mode of the invention, there is also provided the step of gaining access to the treatment site with the guidewire by steering the guidewire into place using radiographic guidance.

In accordance with a further mode of the invention, there are also provided the steps of placing the catheter into the relatively flexible state by changing a temperature of the stiffness device with the temperature-changing device to at least approximately 115° F. and placing the catheter into the relatively stiff state by changing a temperature of the stiffness device with the temperature-changing device to approximately body temperature.

With the objects of the invention in view, there is also provided a method for operating a controllable stiffness catheter to treat atrial fibrillation. A controllable stiffness catheter is provided and has a shaft having a distal end, a stiffness sheath, and an access lumen, a heater inside the stiffness sheath, a non-metallic binder filling the stiffness sheath containing the heater to at least partially surround and thermally contact the heater, the non-metallic binder being relatively solid at or below body temperature and at least partially melting and relatively softened above body temperature, the shaft being in a relatively stiff state when the binder is at or below body temperature and in a relatively flexible state when above body temperature, a power connection selectively supplying power to the heater to change a stiffness of the shaft between the relatively stiff state when the heater is not powered and the relatively flexible state when the heater is powered, and a radiofrequency (RF) energy supply device having at least a portion disposed at the distal end of the shaft for selectively supplying RF energy from the distal end. Power is applied to the heater to place the shaft in the relatively flexible state. The shaft traverses a passage of a body in the relatively flexible state to deliver the distal end of the catheter to a cardiac tissue treatment site and to physically contact the RF energy supply device with the treatment site. Power is removed from the heater to place the catheter into the relatively stiff state and to substantially maintain a current shape of the shaft in the body and at least a portion of the distal end in contact with the treatment site and RF energy is delivered to the treatment site from the RF energy supply device.

In accordance with an added mode of the invention, there are provided the steps of placing the catheter into the relatively flexible state by changing a temperature of the heater to a first temperature and placing the catheter into the relatively stiff state by changing a temperature of the heater to a second temperature different from the first temperature.

In accordance with an additional mode of the invention, the first temperature is higher than the second temperature.

In accordance with yet another mode of the invention, the second temperature is approximately at body temperature and the first temperature is at least 10 degrees Fahrenheit greater than the second temperature.

In accordance with yet a further mode of the invention, the second temperature is approximately 105° F. and the first temperature is at least approximately 115° F.

With the objects of the invention in view, there is also provided a method for delivering a selectively articulated catheter to a treatment site. A guidewire is extended to a treatment site in a body. A controllable articulation catheter is provided and has a shaft having a stiffness sheath and an access lumen, an articulation control device disposed at the stiffness sheath and being in a non-articulating state at or below a first temperature and being in an articulating state at or above a second temperature, the articulation control device having a non-metallic binder that is at least partially melted during the articulating state, a temperature-changing device in thermal contact with the articulation control device, the temperature-changing device changing a temperature of the articulation control device at least from below the first temperature to above the second temperature, and a power controller electrically connected to the articulation control device and selectively supplying power to the temperature-changing device to change a stiffness of the articulation control device between the non-articulating state and the articulating state. While supplying power to the temperature-changing device to place the articulation control device in the articulating state, the catheter is threaded along the guidewire up to the treatment site and is pressed adjacent the treatment site to articulate the shaft into at least one of a desired shape and a desired orientation. Power is removed from the temperature-changing device to place the articulation control device in the non-articulating state without straightening the shaft and, thereby, substantially maintain at least one of the desired shape and the orientation of the shaft.

In accordance with again another mode of the invention, with the catheter in the non-articulating state, the guidewire is distally extended through the treatment site to create a breach at the treatment site.

In accordance with again a further mode of the invention, there are provided the steps of withdrawing the catheter from the guidewire while leaving the guidewire in the breach and advancing a second prosthesis implanting catheter different from the catheter over the guidewire and through the breach to implant a prosthesis at the treatment site.

In accordance with again an added mode of the invention, the second prosthesis implanting catheter is a balloon expanding catheter and the prosthesis is a stent surrounding a balloon, and which further comprises expanding the balloon to dilate the treatment site and place the stent within the dilated breach.

In accordance with again an additional mode of the invention, the second prosthesis implanting catheter is a sheath delivery catheter and the prosthesis is a stent compressed within a sheath of the sheath delivery catheter, and which further comprises withdrawing the sheath to permit expansion of the stent and dilation of the breach.

In accordance with still another mode of the invention, the treatment site is a Chronic Total Occlusion.

In accordance with still a further mode of the invention, with the catheter in the non-articulating state, the guidewire is entirely removed and replaced with a breaching tool and the breaching tool is distally extended through the treatment site to create a breach at the treatment site.

In accordance with still an added mode of the invention, with the catheter in the non-articulating state, a tool is slid distally over the catheter at a proximal end of the catheter and extending the tool over the catheter to the treatment site.

In accordance with still an additional mode of the invention, at least a portion of a radiofrequency (RF) energy device is provided at a distal end of the catheter for selectively supplying RF energy from the distal end and, after placing the catheter into the non-articulating state, the RF energy device physically contacts the treatment site and RF energy is delivered to the treatment site from the RF energy device.

In accordance with another mode of the invention, after placing the catheter into the non-articulating state, a radiofrequency (RF) energy device traverses to a distal end of the catheter for selectively supplying RF energy from the distal end and RF energy is delivered to the treatment site from the RF energy device.

In accordance with a further mode of the invention, after placing the catheter into the non-articulating state, the guidewire is removed to empty the guidewire lumen, a radiofrequency (RF) energy device traverses to a distal end of the catheter for selectively supplying RF energy from the distal end, the RF energy device physically contacts the treatment site, and RF energy is delivered to the treatment site from the RF energy device.

In accordance with an added mode of the invention, before placing the catheter into the non-articulating state, a radiofrequency (RF) energy device traverse to a distal end of the catheter for selectively supplying RF energy from the distal end and, after placing the catheter into the non-articulating state, RF energy is delivered to the treatment site from the RF energy device.

In accordance with another mode of the invention, before placing the catheter into the non-articulating state, the guidewire is removed to empty the guidewire lumen and a radiofrequency (RF) energy device traverses through the guidewire lumen to a distal end of the catheter for selectively supplying RF energy from the distal end and, after placing the catheter into the non-articulating state, the RF energy device physically contacts the treatment site and RF energy is delivered to the treatment site from the RF energy device.

With the foregoing and other objects in view, there is provided, a controllable stiffness catheter comprising a shaft comprising an inner sheath defining an access lumen, an outer sheath surrounding the inner sheath and defining an annulus therebetween, the annulus having a vacuum connection at which a vacuum is applied to the annulus, and a mechanical stiffener disposed at least at a portion of the annulus.

In accordance with another feature, the annulus comprises a proximal portion having a vacuum connection at which a vacuum is applied to the annulus and a closed distal portion.

In accordance with a further feature, there is provided a vacuum device fluidically connected to the vacuum connection and configured to apply a vacuum to the annulus.

In accordance with an added feature, the mechanical stiffener is disposed outside the inner sheath.

In accordance with an additional feature, the mechanical stiffener is disposed inside the outer sheath.

In accordance with yet another feature, the mechanical stiffener is at least one of granular aluminum oxide and granular silica.

In accordance with yet a further feature, when vacuum is applied to the vacuum connection, pressure is lowered within the annulus and the outer sheath compresses the grains of the mechanical stiffener to stiffen the shaft at least at the portion at which the mechanical stiffener is disposed without straightening the shaft at the portion.

In accordance with yet an added feature, when vacuum is applied to the vacuum connection, pressure is lowered within the annulus and the shaft is stiffened at least at the portion at which the mechanical stiffener is disposed without straightening the shaft at the portion.

In accordance with yet an additional feature, the inner sheath has an outside surface, the outer sheath has an inside surface, and the mechanical stiffener comprises a surface roughening on at least one of the outside surface of the inner sheath and the inside surface of the outer sheath.

In accordance with again another feature, a magnitude of a pressure change between an outside of the catheter and the interior of the annulus affects stiffness of the shaft such that, as the pressure difference increases, the stiffness at least at the portion increases.

In accordance with again a further feature, the mechanical stiffener stiffens at least the portion to a relatively stiff state when vacuum is applied at the vacuum connection and softens the portion to a relatively soft state when the vacuum is released from the vacuum connection.

In accordance with again an added feature, the inner sheath is substantially concentric with the outer sheath.

In accordance with again an additional feature, the inner sheath is off-center within the outer sheath.

In accordance with still another feature, the outer sheath has an inner wall and the inner sheath is disposed at the inner wall of the outer sheath.

In accordance with still a further feature, the outer sheath is of polyurethane and the inner sheath is of PTFE.

In accordance with still an added feature, an entire length of the shaft is controllable in stiffness.

In accordance with still an additional feature, some of the shaft is controllable in stiffness.

In accordance with another feature, the portion is a distal 20 cm of the shaft.

In accordance with a further feature, the mechanical stiffener is subdivided into different stiffening segments.

In accordance with an added feature, the shaft has a proximal portion and which further comprises a luer fitting at the proximal portion.

In accordance with an additional feature, the luer fitting provides access to the access lumen.

In accordance with yet another feature, the luer fitting provides access to the annulus.

In accordance with a concomitant feature, a diameter of the access lumen is at least 0.4064 mm and an outer diameter of the shaft is no greater than 1.651 mm.

Other features that are considered as characteristic for the invention are set forth in the appended claims.

Although the invention is illustrated and described herein as embodied in a catheter with controllable stiffness and method for operating a selective stiffening catheter, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

Advantages of embodiments the present invention will be apparent from the following detailed description of the preferred embodiments thereof, which description should be considered in conjunction with the accompanying drawings in which.

DETAILED DESCRIPTION OF THE PREFERRED EMBODIMENTS

Figure 1:
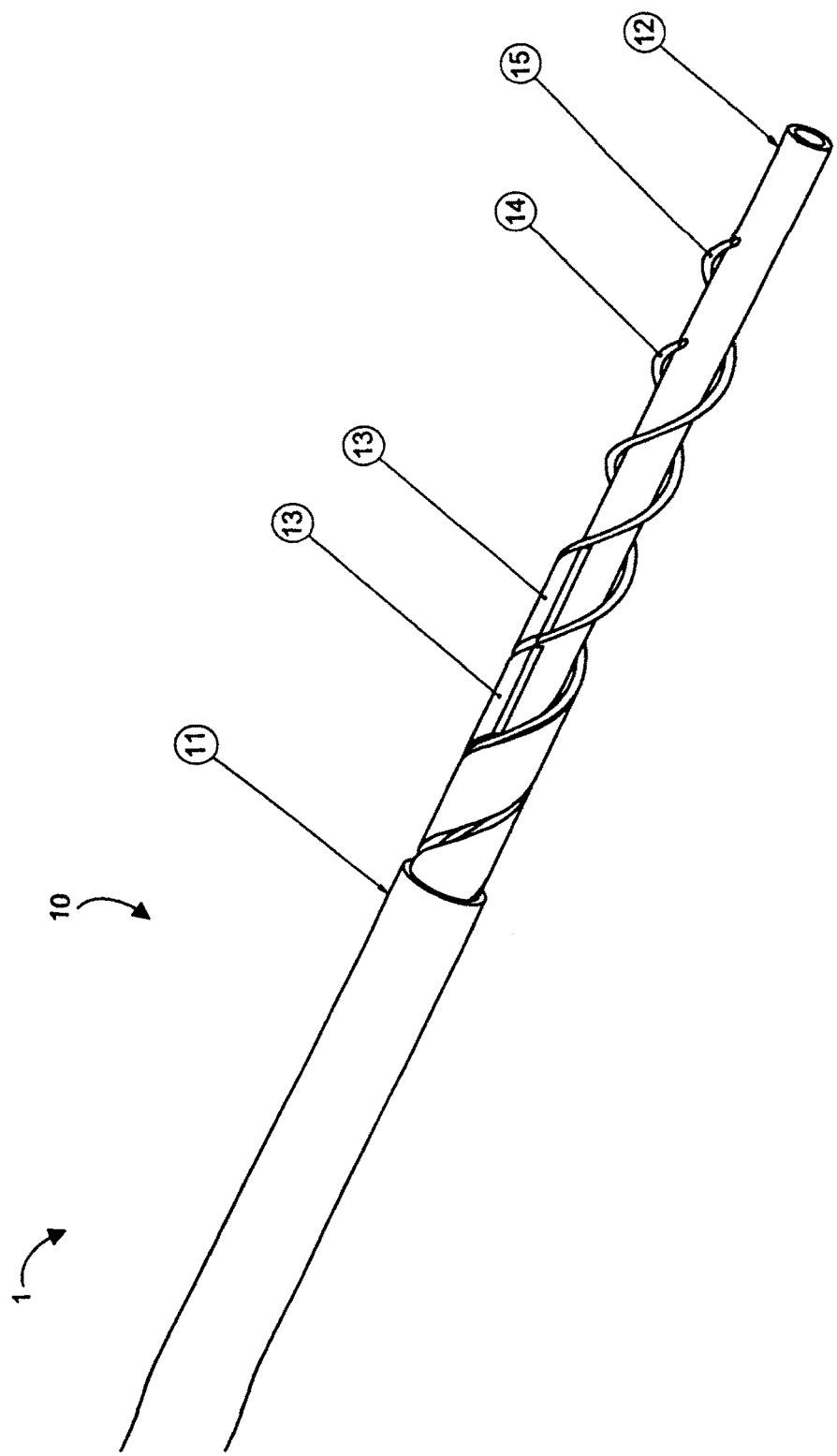
FIG. 1 is a fragmentary, enlarged perspective view of a distal end of a shaft of a catheter according to the invention.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

While the specification concludes with claims defining the features of the invention that are regarded as novel, it is believed that the invention will be better understood from a consideration of the following description in conjunction with the drawing figures, in which like reference numerals are carried forward.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

Referring now to the figures of the drawings in detail and first, particularly to FIG. 1 thereof, there is shown a distal portion of a shaft 10 of an exemplary embodiment of a catheter 1 according to the invention. The shaft 10 is configured with an outer sheath 11 made of a polymer tube such as polyurethane and an inner sheath 12 made of a polymer tube such as PTFE. The inner sheath 12 is assembled substantially concentrically with the outer sheath 11. The annulus between the inner and outer sheaths 12, 11 is filled with a stiffness device, in particular, at least one carbon fiber tow 13 (preferably, 2 to 4 tows 13 extending longitudinally in a helix or braided) impregnated with a binder such as a low-melt-point paraffin or microcrystalline wax or other temperature dependent phase change material. At body temperature, the binder is a solid and, therefore, the carbon fiber tow 13 behaves substantially as a solid carbon fiber rod. (As used herein, "body temperature" is defined to be approximately 40.5° C. (105° F.) or below). In such a condition, the catheter is stiff due the high modulus of the carbon fibers.

It is noted that concentricity is not a requirement. In another exemplary embodiment of the catheter 1 of the present invention, the inner sheath 12 can merely be off-center or the inner sheath 12 can be disposed at the inner wall of the outer sheath 11. In the latter orientation, the space in which the stiffness device resides is somewhat crescent-shaped.

Figure 2:
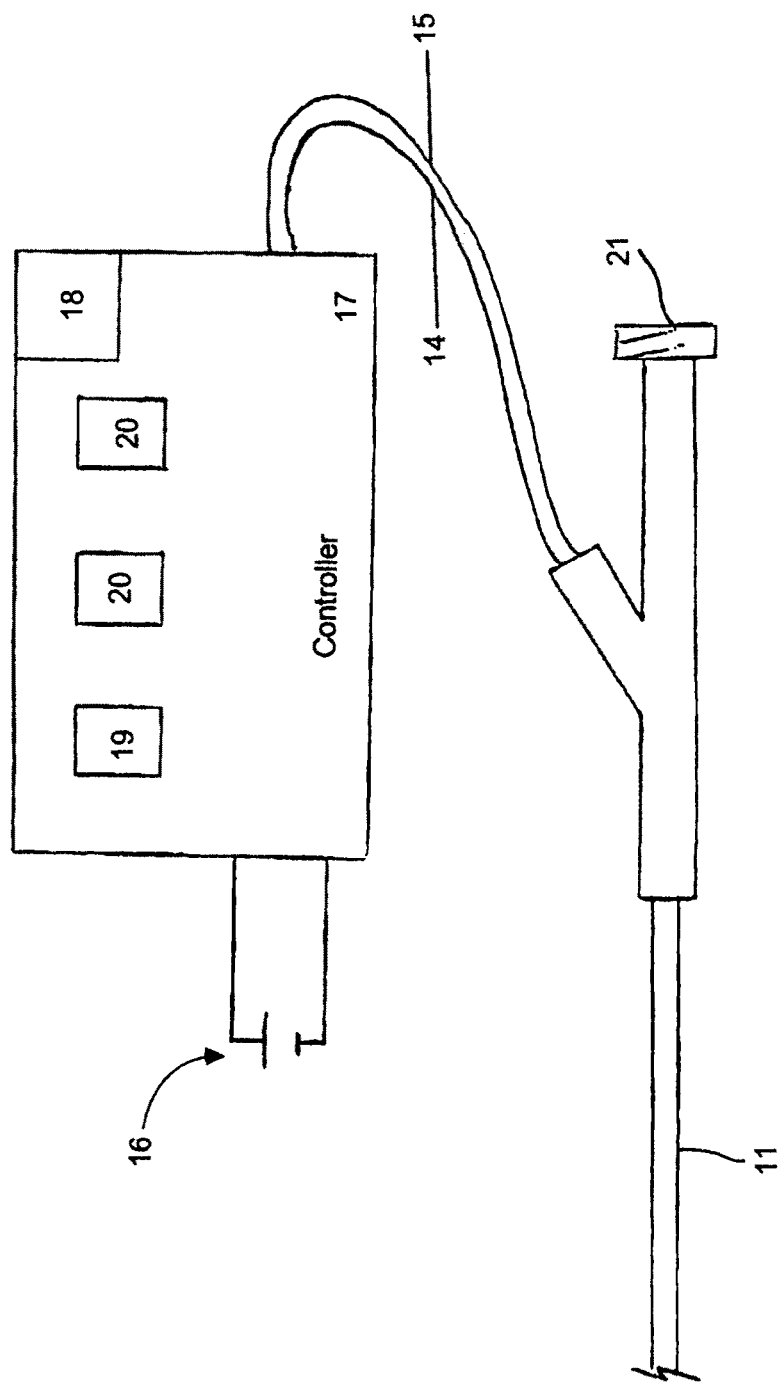
FIG. 2 is a block and schematic circuit diagram and a diagrammatic side elevational view of a proximal end of the catheter according to the invention.

In one exemplary embodiment, an electrical conductor 14, such as insulated copper wire, makes electrical contact with the distal end(s) of the carbon fiber tow(s) 13 and runs from the distal end of the catheter 1 to the proximal end of the catheter 1. The proximal end(s) of the carbon fiber tow(s) 13 makes contact with a second electrical conductor 15, such as copper wire, which extends to the proximal end of the catheter 1 at which resides a power supply 16 (e.g., a battery or an electric mains) and a controller 17 as shown in FIG. 2. The proximal ends of the two conductors 14, 15 are electrically connected to the power supply 16 through the controller 17. These features make up a simple electrical circuit with the carbon fiber tow(s) acting like a resistor in the circuit. When voltage is applied to the two electrical conductors 14, 15, current flows through the circuit 13, 14, 15 and resistively heats the carbon fiber tow(s) 13. When the tow 13 is heated to raise the temperature of the binder above a binder transition temperature, the binder softens (which can include a partial or a full melt) and allows the individual carbon fibers to move with respect to each other, thereby making the catheter shaft more flexible than before. (As used herein, the binder transition temperature is at or above approximately 46° C. (115° F.).) When the voltage is removed from the circuit 13, 14, 15, the binder cools and solidifies. Thus, the catheter shaft 10 stiffens to its then constrained shape. This heating and cooling can be done repeatedly—making the catheter 1 flexible when navigating through a tortuous path and stiff when placed in a position for use, for example.

Another exemplary embodiment of the catheter 1 according to the invention is similar to that illustrated in FIG. 1 but, instead of a concentric configuration, the shaft 10 is constructed of a first hollow sheath 11 made of a polymer tube such as polyurethane and a second hollow sheath 12 made of a polymer tube such as PTFE. The first sheath 11 is assembled next to and outside of the interior of the second sheath 12 such that a cross-section of the two conduits is shaped like the number eight. The entire core of the second sheath 12, therefore, can be used to house the stiffness device 13.

Electrical power for supplying a voltage or current can be provided, for example, by at least one battery 16. This battery 16 can be connected to the conductors 14, 15 through the controller 17, which is configured to limit heating of the binder by limiting current through the circuit 13, 14, 15. Such current limiting can be achieved by using a Proportional-Integral-Derivative (PID) controller whereby a standard feedback loop measures the "output" of the process and controls the "input", with a goal of maintaining the output at a target value, which is called the "setpoint". Such a current-sensing controller, for example, could make the initial current through the circuit 13, 14, 15 high enough to achieve a rapid melt and, thus, a rapid softening, with a subsequent decrease and leveling in the current to just maintain the melt. A thermocouple 18 can be added to actively monitor temperature of the melt. A control switch 19 and indicator LEDs 20 are added to the handle of the catheter 1 to give control and feedback to the user.

The entire length of the catheter 1 can be controllable in stiffness or just a portion of it can be controlled. In the case of a coronary catheter, the distal 20 cm or so can be controllable. The remainder of the catheter 1 can be constructed to have a stiffness sufficient to deliver the controllable portion to the coronary arteries. In such an embodiment, the stiffness device 13 is only present in the distal quarter of the shaft, for example, and one conductor 14 is electrically connected to the distal end of the stiffness device 13 (located at approximately the distal end of the shaft) and the other conductor 15 is electrically connected to a point on the shaft approximately three-quarters of the way to the distal end of the stiffness device 13.

The connection of conductors 14, 15 need not only be at the two ends of the stiffness device 13. Additional non-illustrated conductors can be electrically connected to different places along a single stiffness device 13 that extends the entire length of the catheter 1 to, thereby, subdivide the stiffness device 13 into different stiffening segments. The proximal ends of each of these additionally conductors are electrically connected to the controller 17. Accordingly, only a portion or a set of portions of the stiffness device 13 can be softened depending upon which conductors are energized. Alternatively, the stiffness device 13 can be a set of tows 13 having different lengths with two conductors connected respectively to each tow.

In any embodiment of the conductors 14, 15 and the stiffness device 13, the conductors should be electrically isolated from one another. Even if one conductor contacts a first end of all of a plurality of stiffness devices 13, the other conductors connected to the second end of each stiffness device must be electrically isolated from one another and the one conductor contacting the first end.

FIG. 1 shows a plurality of carbon tows 13 and distal conductors 14, 15 wound around the inner sheath 12. The pitch and the quantity of the carbon fiber tows 13, and the properties of the binder, can be adjusted to affect the final stiffness of the catheter 1. A stiffer binder or the addition of more carbon fiber would lead to a stiffer catheter and a less stiff binder or the subtraction of carbon fiber would lead to a less stiff catheter. A change in the pitch of the wind along the length of the catheter 1 would also vary the stiffness along its length.

The carbon fiber tows 13 can also be oriented longitudinally as rods without wrapping them around the inner sheath 12. Or, a hollow braid of the carbon fiber tows 13 can be made to surround the inner sheath 12. The distal conductor(s) 14, 15 could be included anywhere along the in the rods or braid if desired.

A luer fitting 21 is located at the proximal end of the catheter 1. This fitting 21 provides access to the central lumen of the catheter, for example, for a CTO-piercing tool. A hemostasis valve can be connected to the fitting 21, for example, while the catheter is in use.

In another embodiment of the stiffness device, a mixture of shorter discontinuous fibers such as chopped carbon fiber or fiberglass and binder can be used instead of impregnated continuous carbon fiber tows 13. In such a case, the fibers would no longer be used as the resistive heating measure. Heating of the binder can be achieved by wrapping the inner sheath 12 with a resistive heating element, such as Nickel/Chromium (e.g., NICHROME®) wire. In such a configuration, the wire passes the current and becomes warm, thus heating the surrounding fiber-loaded binder.

In the case of a coronary version of the catheter, the lumen diameter of the inner sheath is, at a minimum, 0.4064 mm (0.016") to ensure free passage of 0.3556 mm (0.014") diameter steerable coronary guidewires. It is preferred for the outer diameter of the catheter to be no greater than 1.651 mm (0.065") to be compatible with an inner diameter of a standard 6 French coronary guide catheter (minimum inner diameter 1.7272 mm (0.068")). Larger or smaller versions can be constructed to suit specific needs.

Figure 3:
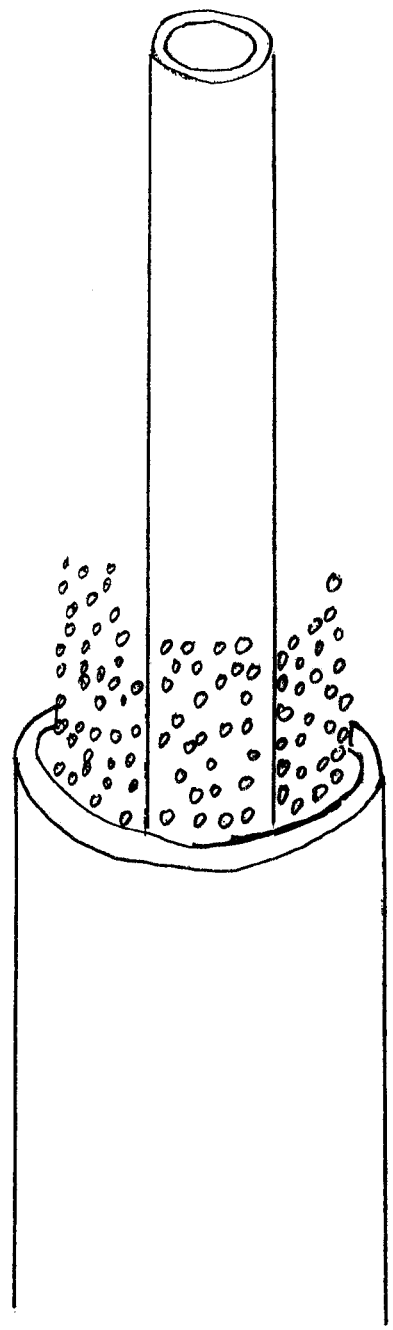
FIG. 3 is a fragmentary, enlarged, cut-away, perspective view of a distal end an alternative embodiment of the catheter according to the invention.
Figure 4:
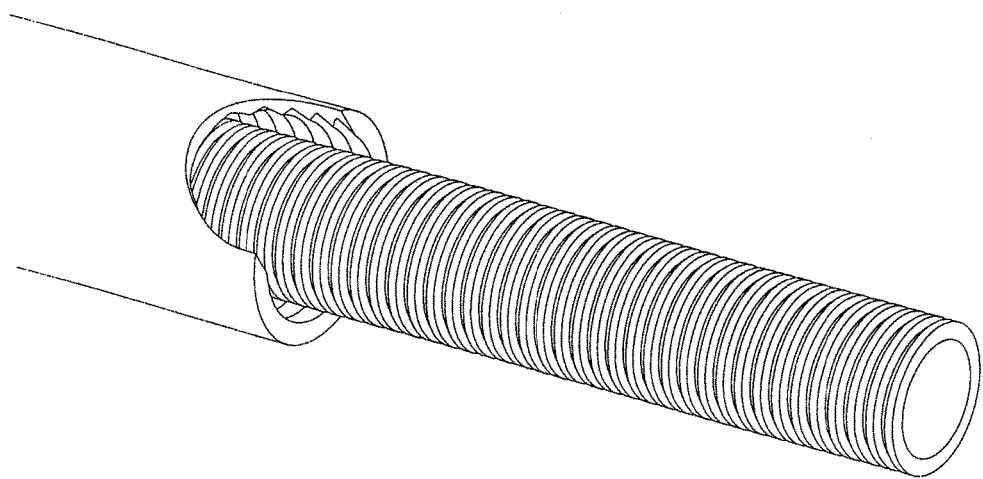
FIG. 4 is a fragmentary, enlarged, cut-away, perspective view of a distal end a further alternative embodiment of the catheter according to the invention.

The catheter can also be stiffened using mechanical measures. The annulus between the inner and outer sheaths can be filled with a fine granular substance, such as aluminum oxide or silica, as shown in FIG. 3. In its flexible state, the fine grains are loose and slide past each other as the catheter is flexed. When vacuum is applied to the annulus, however, the pressure is lowered inside the annulus and the flexible outer sheath begins to compress the grains of the filler together from the urging of the higher pressure outside the catheter. Under such compression, the grains are forced against each other and interlock, no longer sliding past each other and, thus, stiffening the catheter without straightening it. The magnitude of the pressure change between the outside of the catheter and the interior of the annulus affects the catheter stiffness: a small pressure difference (lower vacuum) for a more flexible catheter, a large pressure difference (higher vacuum) for a stiffer catheter. It is clear to see that the catheter could have multiple independent zones that could each be controlled by a different level of vacuum, thus, illustration of this feature is not necessary to understand the present invention. This allows the catheter to be stiff in some zones, and more flexible in others. Such stiffening could also be accomplished without using the granular substance by substituting a rough surface (such as ridges, grooves, bonded grit and combinations thereof) on the outside of the inner sheath and on the inside of the outer sheath as shown in FIG. 4. In its flexible state, the two rough surfaces do not engage each other substantially. When vacuum is applied, the outer sheath is compressed, and the rough surface on the inside of the outer sheath begins to engage the rough surface on the outside of the inner sheath thereby stiffening the catheter.

The following text outlines exemplary procedures for using the catheter 1 of the present invention to pass a CTO.

First, a flexible, steerable guidewire is precisely controlled by the physician and steered into place at a treatment site in a body using, for example, radiographic guidance. Once the guidewire is in place, the catheter 1 of the present invention can be advanced over the guidewire. It is understood that body pathways can be quite tortuous and are made of soft and delicate tissues. This is especially true in the vasculature, in particular, in vessels of the brain and the coronary arteries. Therefore, using the catheter 1 to gain access to the treatment site in the body most likely requires that the catheter 1 start as being flexible to conform to and follow the natural anatomical pathways as it is advanced to the site.

In the case of a CTO, the guidewire is advanced only up to the blockage. Then, the access lumen 12 (whether inside the stiffness lumen 11 or outer sheath 11) is threaded on the guidewire. The catheter 1 is in its softened state or is caused to enter its softened state so that the catheter 1 can be threaded along the guidewire up to the CTO. At the point where the catheter 1 is near the CTO, the catheter 1 is caused to become stiff (without straightening). In the stiff state, a CTO-opening tool will be used to open the CTO. For example, the CTO-opening tool can be the guidewire itself. Alternatively, a CTO-opening tool can be inserted through the access lumen 12 and into the CTO. If the tool is a device entirely separate from the catheter 1, the guidewire can be removed from the catheter 1 and the CTO-opening tool can be threaded through the access lumen 12. Preferably, the CTO-opening tool is hard (but flexible to traverse the catheter 1) and has a sharp distal end.

The guidewire or tool is pressed through the CTO with the stiffened catheter 1 efficiently transmitting the thrust loads to the tool as the CTO is providing resistance to puncture. Once the guidewire/tool is across the CTO, the guidewire/tool can be used to guide another device that will open and fix the blockage. To remove the catheter 1, first, the catheter 1 is caused to soften. After softening, the catheter 1 is removed and the guidewire/tool is left in the position passed through the CTO. A low profile balloon catheter, for example, is advanced over the guidewire/tool and through the lesion. The balloon is expanded to dilate the lesion. A stent can, then, be placed in the lesion to fix the CTO.

With use of the catheter according to the invention, the guidewire/tool will not flex away from the treatment site when pushed and provides great increases in feel, control, and thrust. Such characteristics aid in the successful crossing of difficult-to-cross lesions and provide an opportunity to cross CTOs.

Atrial fibrillation is the most common heart arrhythmia in the world, affecting over 2.5 million people in the United States alone. In atrial fibrillation, the electrical signals in the atrial (upper) chambers of the heart are chaotic. In addition, the atrial electrical impulses that reach the ventricles (lower heart chambers) often arrive at irregular intervals.

Ablation of cardiac tissue, to create scar tissue that poses an interruption in the path of the errant electrical impulses in the heart tissue, is a commonly performed procedure to treat cardiac arrhythmias. Such ablation may range from the ablation of a small area of heart tissue to a series of ablations forming a strategic placement of incisions in both atria to stop the conduction and formation of errant impulses.

Ablation has been achieved or suggested using a variety of techniques, such as freezing through cryogenic probe, heating through RF energy, surgical cutting, and other techniques. As used here, "ablation" means the removal or destruction of the function of a body part, such as cardiac tissue, regardless of the apparatus or process used to carry out the ablation. Also, as used herein, "transmural" means through the wall or thickness, such as through the wall or thickness of a hollow organ or vessel.

Ablation of cardiac tissue may be carried out in an open surgical procedure, where the breastbone is divided and the surgeon has direct access to the heart, or through a minimally invasive route, such as between the ribs or through a catheter that is introduced through a vein and into the heart. Types of ablation for atrial fibrillation include Pulmonary vein isolation ablation (PVI Ablation or PVA), cryoablation (freezing), and atrioventricular (AV) node ablation with pacemakers.

Prior to any ablation, the heart typically is electronically mapped to locate the point or points of tissue that are causing the arrhythmia. With minimally invasive procedures such as through a catheter, the catheter is directed to the aberrant tissue, and an electrode or cryogenic probe is placed in contact with the endocardial tissue. RF energy is delivered from the electrode to the tissue to heat and ablate the tissue (or the tissue may be frozen by the cryogenic probe), thus eliminating the source of the arrhythmia.

Common problems encountered in this procedure are difficulty in precisely locating the aberrant tissue, and complications related to the ablation of the tissue. Locating the area of tissue causing the arrhythmia often involves several hours of electrically "mapping" the inner surface of the heart using a variety of mapping catheters, and once the aberrant tissue is located, it is often difficult to position the catheter and the associated electrode or probe so that it is in contact with the desired tissue.

The application of either RF energy or ultra-low temperature freezing to the inside of the heart chamber also carries several risks and difficulties. It is very difficult to determine how much of the catheter electrode or cryogenic probe surface is in contact with the tissue since catheter electrodes and probes are cylindrical and the heart tissue cannot be visualized clearly with existing fluoroscopic technology. Further, because of the cylindrical shape, some of the exposed electrode or probe area will almost always be in contact with blood circulating in the heart, giving rise to a risk of clot formation.

Clot formation is almost always associated with RF energy or cryogenic delivery inside the heart because it is difficult to prevent the blood from being exposed to the electrode or probe surface. Some of the RF current flows through the blood between the electrode and the heart tissue and this blood is coagulated, or frozen when a cryogenic probe is used, possibly resulting in clot formation. When RF energy is applied, the temperature of the electrode is typically monitored so as to not exceed a preset level, but temperatures necessary to achieve tissue ablation almost always result in blood coagulum forming on the electrode.

Overheating or overcooling of tissue is also a major complication, because the temperature monitoring only gives the temperature of the electrode or probe, which is, respectively, being cooled or warmed on the outside by blood flow. The actual temperature of the tissue being ablated by the electrode or probe is usually considerably higher or lower than the electrode or probe temperature, and this can result in overheating, or even charring, of the tissue in the case of an RF electrode, or freezing of too much tissue by a cryogenic probe. Overheated or charred tissue can act as a locus for thrombus and clot formation, and over freezing can destroy more tissue than necessary. It is also very difficult to achieve ablation of tissue deep within the heart wall.

Other forms of energy have been used in ablation procedures, including ultrasound, cryogenic ablation, and microwave technology. When used from an endocardial approach, the limitations of all energy-based ablation technologies to date are the difficulty in achieving continuous transmural lesions and minimizing unnecessary damage to endocardial tissue. Ultrasonic and RF energy endocardial balloon technology has been developed to create circumferential lesions around the individual pulmonary veins. See e.g., U.S. Pat. No. 6,024,740 to Lesh et al. and U.S. Pat. Nos. 5,938,660 and 5,814,028 to Swartz et al. However, this technology creates rather wide (greater than 5 mm) lesions that could lead to stenosis (narrowing) of the pulmonary veins. The large lesion area can also act as a locus point for thrombus formation. Additionally, there is no feedback to determine when full transmural ablation has been achieved. Cryogenic ablation has been attempted both endocardially and epicardially (see e.g., U.S. Pat. No. 5,733,280 to Avitall, U.S. Pat. No. 5,147,355 to Friedman et al., and U.S. Pat. No. 5,423,807 to Milder, and WO 98/17187, the latter disclosing an angled cryogenic probe, one arm of which is inserted into the interior of the heart through an opening in the heart wall that is hemostatically sealed around the arm by a suture or staples), but because of the time required to freeze tissue, and the delivery systems used, it is difficult to create a continuous line, and uniform transmurality is difficult to verify.

International Publications WO99/56644 and WO99/56648 disclose an endocardial ablation catheter with a reference plate located on the epicardium to act as an indifferent electrode or backplate that is maintained at the reference level of the generator. Current flows either between the electrodes located on the catheter, or between the electrodes and the reference plate. It is important to note that this reference plate is essentially a monopolar reference pad. Consequently, there is no energy delivered at the backplate/tissue interface intended to ablate tissue. Instead, the energy is delivered at the electrode/tissue interface within the endocardium, and travels through the heart tissue either to another endocardial electrode, or to the backplate. Tissue ablation proceeds from the electrodes in contact with the endocardium outward to the epicardium. Other references disclose epicardial multi-electrode devices that deliver either monopolar or bipolar energy to the outside surface of the heart.

It is important to note that all endocardial ablation devices that attempt to ablate tissue through the full thickness of the cardiac wall have a risk associated with damaging structures within or on the outer surface of the cardiac wall. As an example, if a catheter is delivering energy from the inside of the atrium to the outside, and a coronary artery, the esophagus, or other critical structure is in contact with the atrial wall, the structure can be damaged by the transfer of energy from within the heart to the structure. The coronary arteries, esophagus, aorta, pulmonary veins, and pulmonary artery are all structures that are in contact with the outer wall of the atrium, and could be damaged by energy transmitted through the atrial wall. CTO crossing is not the only application for the catheter according to the invention. Many other uses are possible.

Where treatment of atrial fibrillation requires the delivery of radiofrequency energy to parts of the heart, the catheter needs to be flexible enough to get to the heart but stiff enough to apply pressure to the heart so that sufficient contact with the tissue is made. If the contact is not sufficient, then charring can occur at the interface between the device and tissue causing a decrease in the efficacy of treatment or even injury.

In one exemplary method, the catheter according to the invention can be used to treat atrial fibrillation by delivering the needed radiofrequency energy to parts of the heart. First, a flexible, steerable guidewire is precisely controlled by the physician and steered into place at a treatment site in a body using, for example, radiographic guidance. Once the guidewire is in place, the catheter 1 of the present invention can be advanced over the guidewire. As set forth above, using the catheter 1 to gain access to the treatment site in the body most likely requires that the catheter 1 start as being flexible to conform to and follow the natural anatomical pathways as it is advanced to the site.

Figure 5:
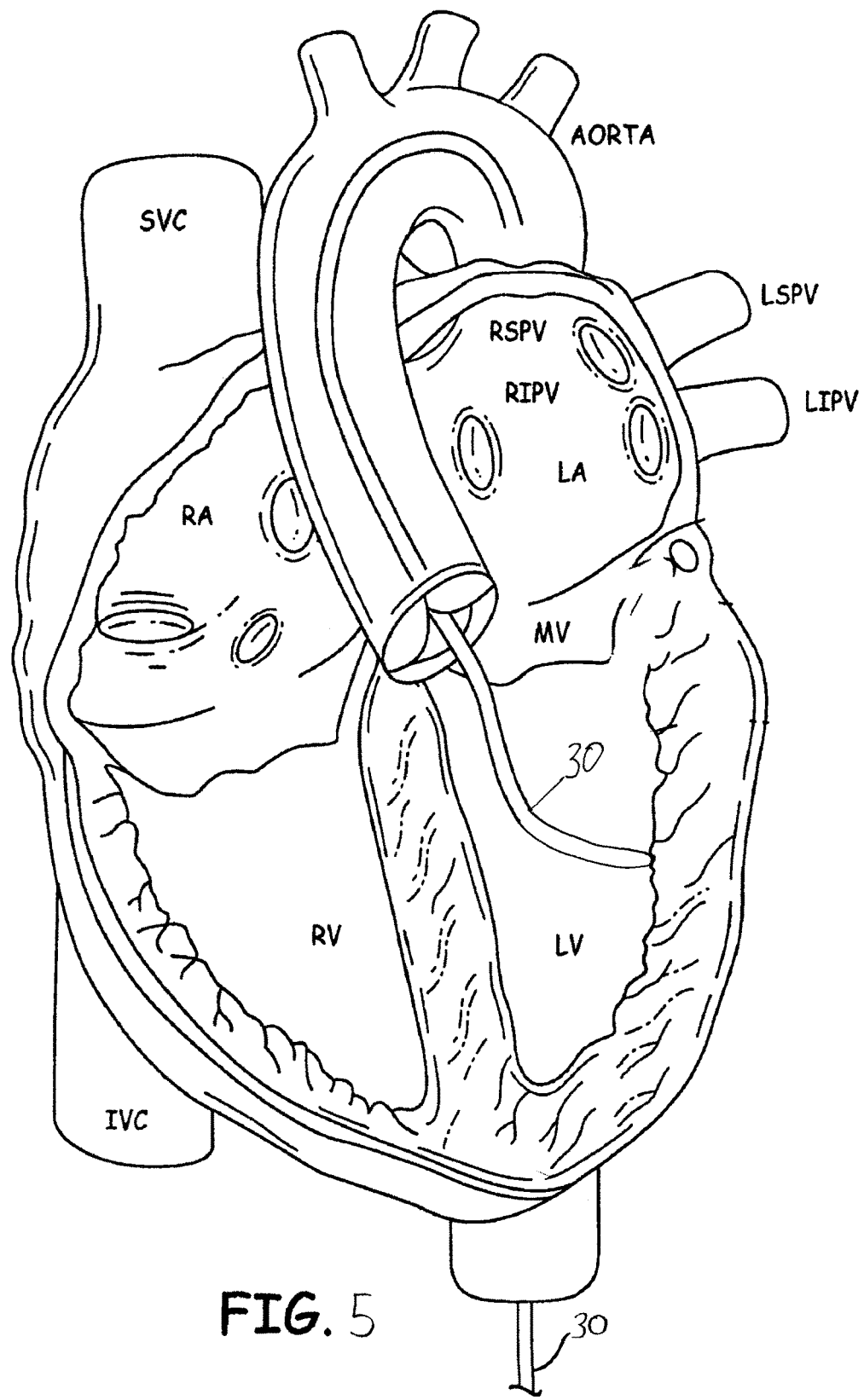
FIG. 5 is a fragmentary, partially cut-away perspective view of a heart with a variflex catheter according to the invention traversing an aorta into the left ventricle.
Figure 6:
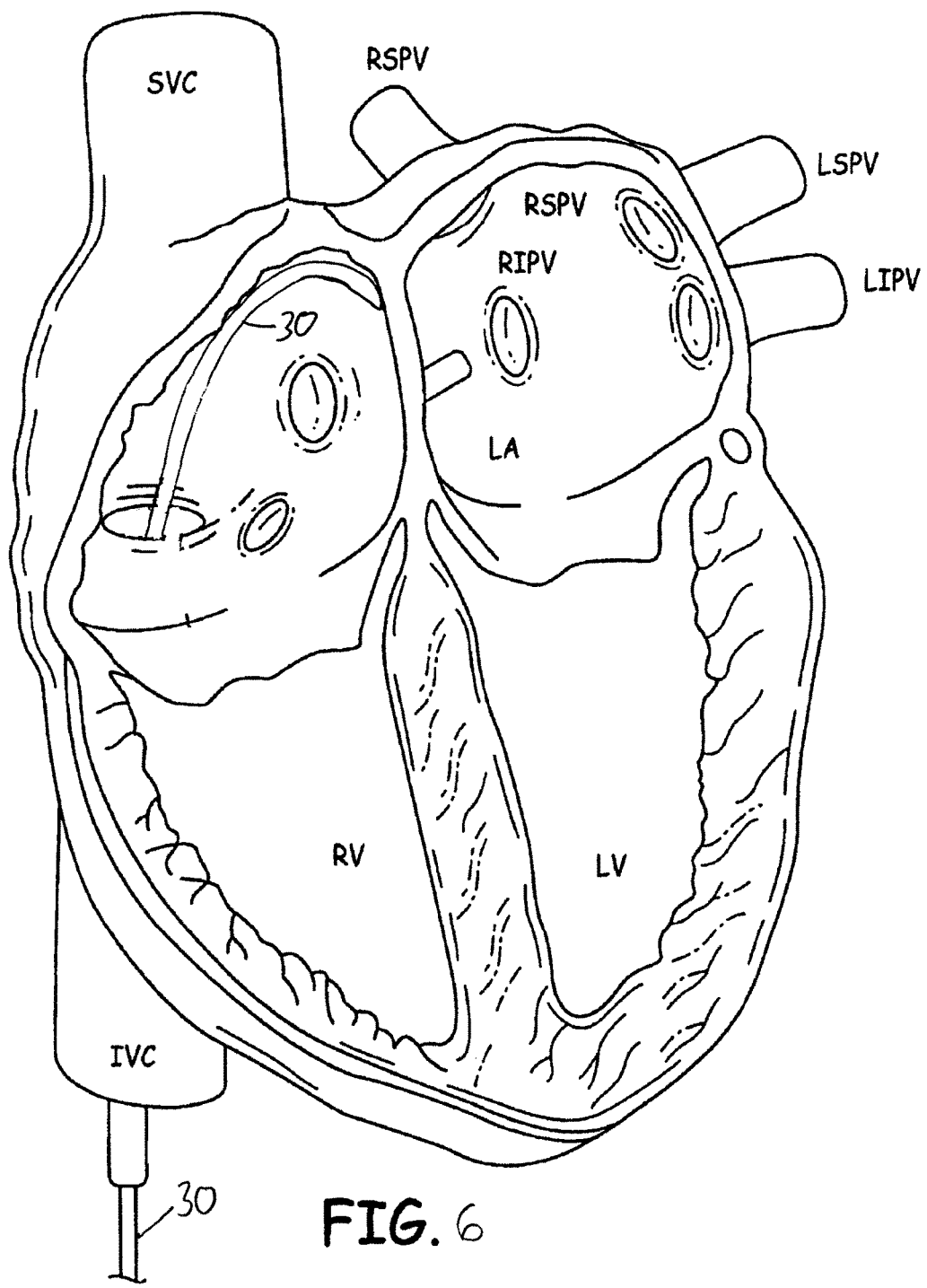
FIG. 6 is a fragmentary, partially cut-away perspective view of a heart with a variflex catheter according to the invention traversing an inferior vena cava into the right atrium.
Figure 7:
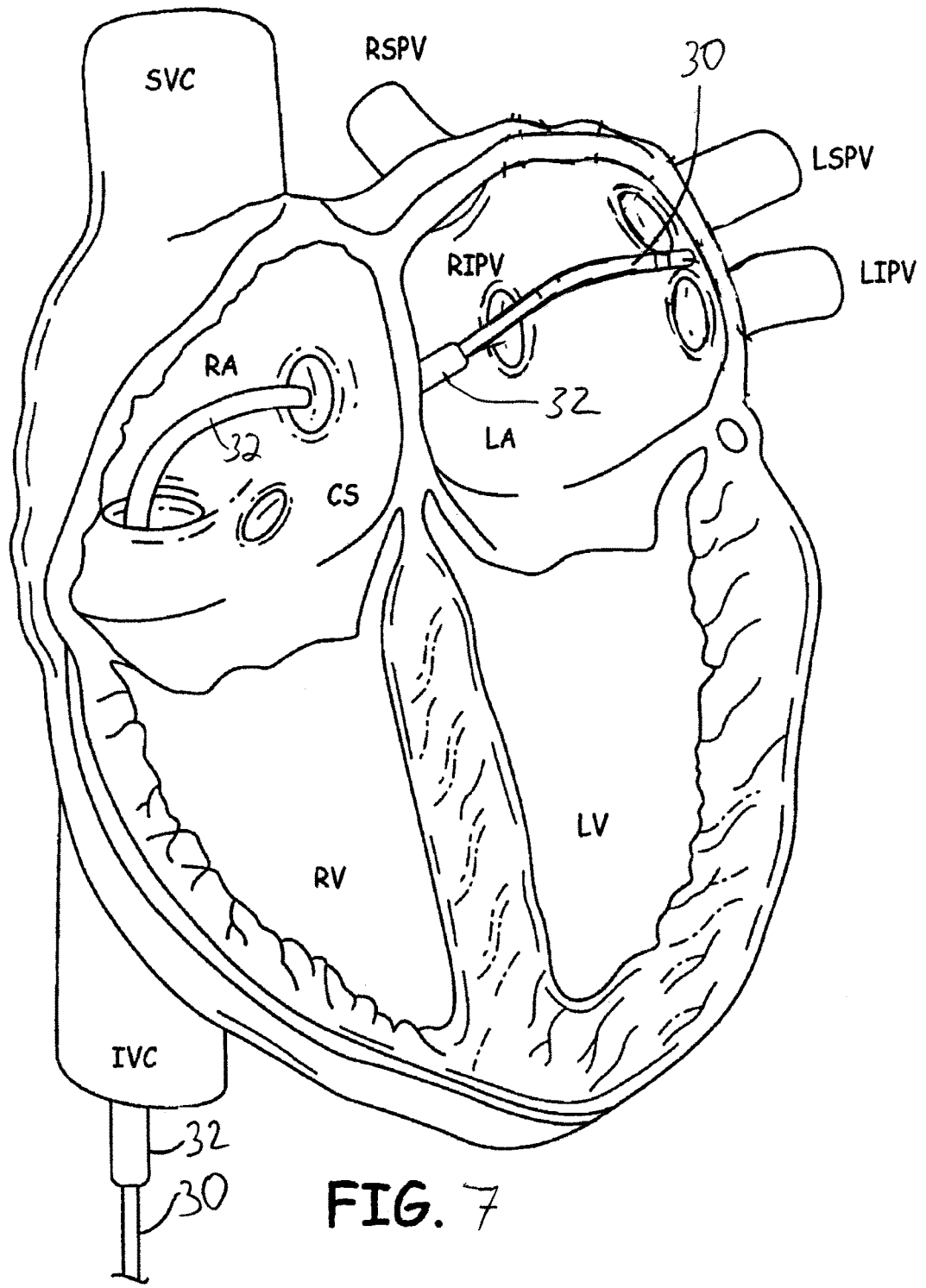
FIG. 7 is a fragmentary, partially cut-away perspective view of a heart with a variflex catheter according to the invention traversing an inter-atrial septum to reach the left atrium.

In the case of a treatment of atrial fibrillation, the guidewire is advanced only up to the cardiac tissue to be treated. Then, the access lumen 12 (whether inside the stiffness lumen 11 or outer sheath 11) is threaded on the guidewire. The catheter 1 is in its softened state or is caused to enter its softened state so that the catheter 1 can be threaded along the guidewire up to the cardiac tissue. At the point where the catheter 1 has contact with the cardiac tissue to be treated, the catheter 1 is caused to become stiff (without straightening). In the stiff state, the portion of the catheter 1 that delivers the radiofrequency energy will be secured at a given contact point. Alignment and contact of the energy imparting area to the cardiac tissue to be treated can be examined and, if satisfactory, the energy can be imparted with increased accuracy to the target tissue. FIGS. 5, 6, and 7 illustrate three exemplary applications for use of the catheter in treating atrial fibrillation. FIG. 5 shows a catheter 30 that is guided through the aorta and into the left ventricle. FIG. 6 illustrates the catheter 30 guided through the inferior vena cava and into the right atrium. FIG. 7 depicts the catheter 30 passing through a puncture device 32 that spans the inter-atrial septum to treat the left atrium. In such a situation, the variflex technology can be used both on the catheter 30 and the puncture device 32.

If the RF energy-delivering tool is a device entirely separate from the catheter 1, the guidewire can be removed from the catheter 1 and the tool can be threaded through the access lumen 12.

Another exemplary embodiment for the catheter according to the invention is where passive articulation is required at the distal treatment end of an atrial fibrillation treatment catheter. Current catheters have active articulation control for reaching different parts of the heart, but such catheters require a cable or cables are pulled at the hand of the user causing the device to flex at the tip in a predetermined shape. The variable flexing (variflex) technology of the catheter according to the invention could be placed on a portion of the atrial fibrillation (AF) catheter. The AF catheter could be so modified and pushed up against cardiac tissue with the variflex section in the flexible condition. Thus allowing the physician to bend the variflex section to any desired position. When the desired position is reached, the variflex section can be stiffened. This process could be used for any medical device that needed controllable articulation, such as gastro-intestinal (GI) instruments, neurological instruments and other vascular instruments.

Yet another exemplary embodiment for the catheter according to the invention is for use as a transeptal sheath, which can be articulated once it is placed into the atrium of a heart in one of two ways. First, the articulation can occur by the passive articulation that is described herein. Second, the articulation can be effected by introducing a pre-formed, pre-bent stylette. In particular, the transeptal sheath is introduced into the atrium in the soft, flexible condition. A pre-bent stylette is inserted inside the sheath in a distal direction until the desired bend of the transeptal sheath inside of the atrium is obtained. The shape of the transeptal sheath is modified by pushing the stylette further in the distal direction, by pulling the stylette proximally, or by rotating the stylette. Once the desired shape is obtained, the transeptal sheath is switched to the stiff condition, thus maintaining the desired shape.

Still a further exemplary embodiment for the catheter according to the invention allows use of a removable implant that includes the variflex technology. The implant has a pre-defined shape for use in the body. The implant is caused to become flexible and, therefore, can be reshaped to a configuration that allows implantation and, when at the site in which it is to be implanted, can be de-energized to harden at the site. The implant can be removed from the energy source and left in the body. In an exemplary embodiment, a spiral variflex stent can be straightened and moved to the implantation site in a straight configuration. When in a desired position at the implantation site, the stent can be caused to spiral into the shape that prevents migration and opens the vessel. It would be left in the implantation position. At a later time, the variflex energizing system could be reconnected to the implant to make it flexible again for removal or replacement.

A first medical area that the catheter according to the invention can be use is cardiovascular. In one application, cardiovascular guiding catheters can be improved upon by using the variflex technology. Such variflex equipped guiding catheters can be inserted into a patient with the guiding catheter, a section of the guiding catheter, or multiple sections of the guiding catheter using the variflex technology of the present invention. Having the variable flexibility makes insertion of the guiding catheter into the target vessel easier, increases the back-up support of the guiding catheter, and substantially prevents migration out of the vessel during use. The guiding catheter is inserted with the variflex section or sections in the soft state and, then, the variflex section or sections would be stiffened when the guiding catheter was placed in the desired position. This would stabilize the tip of the guiding catheter in the target vessel to allow the subsequent passage of devices thru the guide and into the vessel for treatment. After the procedure is completed, the guide can be made soft again for easy removal from the vessel.

A second medical area in which the catheter according to the invention could be used is with stent delivery systems. For example, such delivery systems are improved when the variflex technology of the present invention is disposed on the inner member of the balloon catheter. Such a variflex-equipped delivery system still allows easy insertion by using the catheter in the soft, flexible state. When the stent is positioned at the desired location, the inner member of the balloon catheter is stiffened to prevent the balloon from migrating during stent deployment, assuring accurate placement of stent in a target lesion.

The invention of the instant application can improve balloon angioplasty as well. Using of the variflex technology permits easier navigation through a tortuous vascular system when in the flexible state. The catheter delivering the balloon is stiffened and locked in place relative to the vascular system once the desired location has been reached. Combined with a balloon/stent viewing system such as fluoroscopy, the stent and/or balloon position can be verified and, if needing a different orientation, could be changed by softening and re-hardening the catheter until the desired placement is obtained. Such an improvement gives the physician more precise control for aligning the balloon with the target lesion.

The variflex invention of the instant application can also improve guidewire technology. In such a configuration, the guidewire has a steel or a Nitinol core and the variflex technology is manufactured around the core along its entire length, in a particular section, or in multiple sections. The variflex section/sections is/are softened for insertion of the guidewire into the patient and are hardened once the guidewire is placed in its desired position. This orientation locks the guidewire in place relative to the vascular system.

Figure 8:
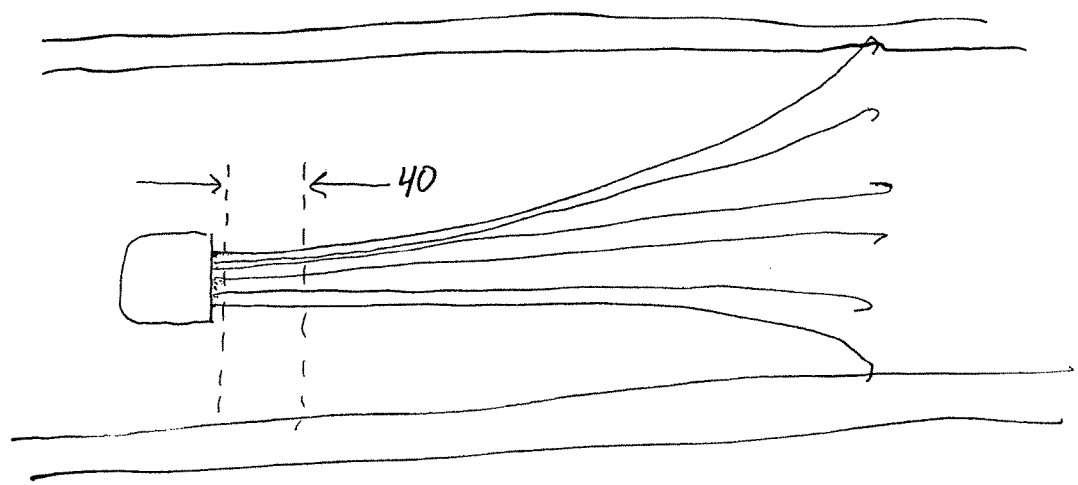
FIG. 8 is a fragmentary, side elevational view of a vena cava filter implanted in a vessel and containing a variflex portion according to the invention in a stiff state.
Figure 9:
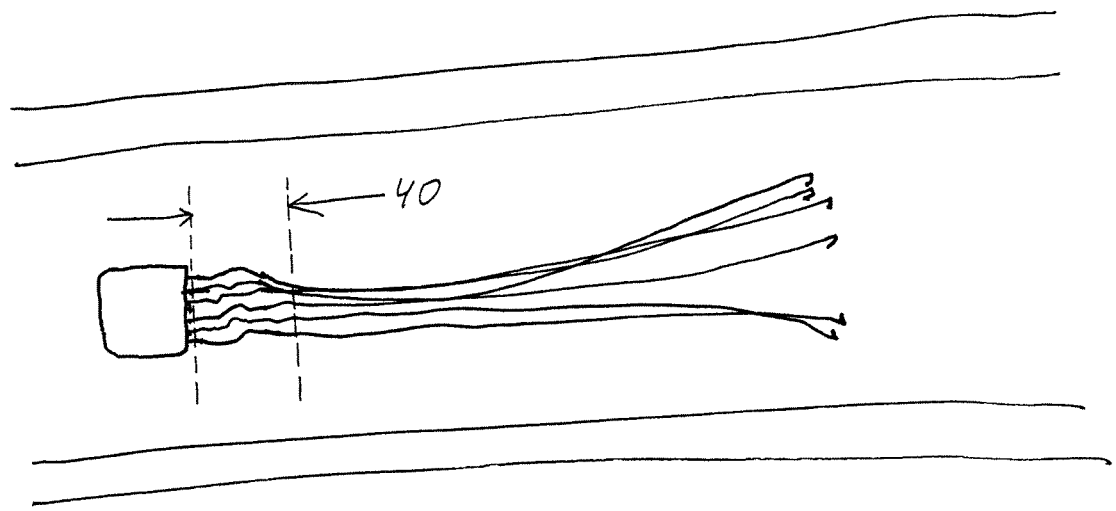
FIG. 9 is a fragmentary, side elevational view of the filter of FIG. 8 with the variflex portion in a soft, flexible state.

The variflex invention of the instant application can also improve blood clot removal technology. For example, a vena cava filter is improved adding a section 40 of the variflex technology to the arms of the device as shown in FIGS. 8 and 9. Such a filter is inserted and left in place with the variflex section in the hardened condition to give the filter legs their desired stiffness for springing outward. In such an implanted state, conventional filters cannot be removed without difficulty or injury. In comparison, a variflex-equipped vena cava filter can be removed. First, a catheter equipped to deliver electrical energy to the variflex section 40 is brought into contact with the filter. The variflex section 40 is made to soften and become flexible to allow the arms of the filter to relax. In such a state, easy removal is possible.

A variflex catheter according to the invention can be used in conjunction with reaching tortuous vascular anatomy with a guidewire. In such an application, the variflex catheter is loaded over the guidewire. The guidewire is inserted into the patient until it became difficult to pass the guidewire. The variflex catheter in its soft condition is, then, inserted over the guidewire close to the guidewire's distal end. The variflex catheter is, then, stiffened and the guidewire is inserted further. The variflex catheter supports the guidewire along its length, thus lessening the damage to the vessels and allowing more force to be exerted at the tip of the guidewire.

Figure 10:
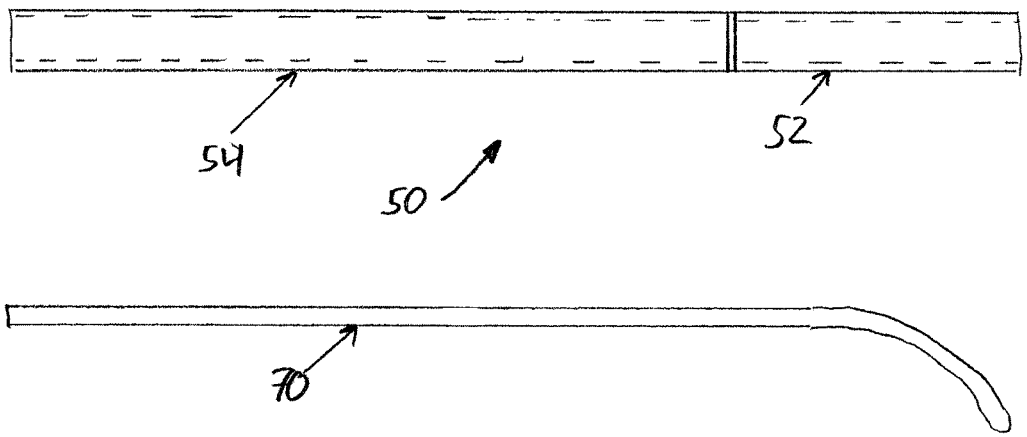
FIG. 10 is a fragmentary, exploded and partially hidden side elevational view of a channel with a variflex distal end and a stylette to be inserted in the channel.
Figure 11:
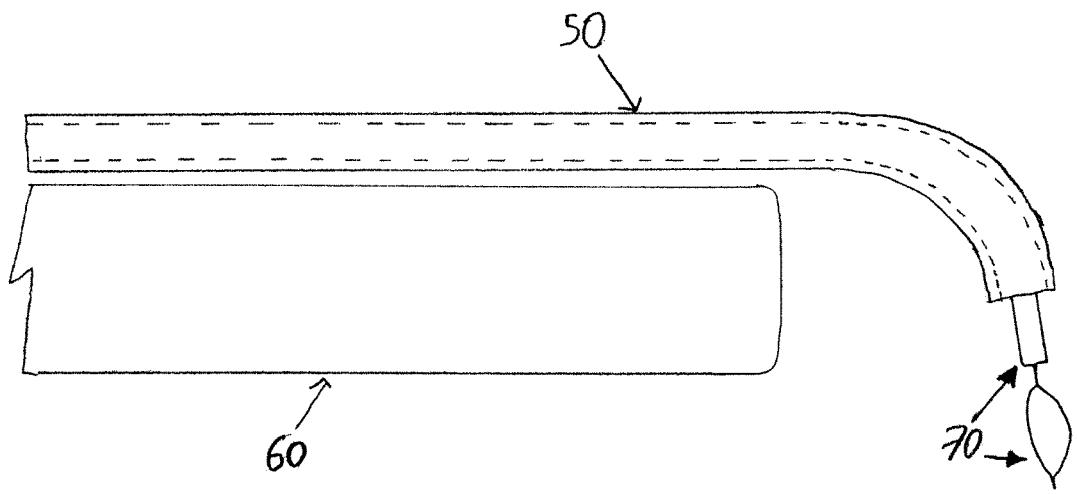
FIG. 11 is a fragmentary, partially hidden side elevational view of an endo scope and an attached channel with a snare device inserted therein.

The variflex invention of the instant application can also be applied to various transgastric surgery applications. In one application, illustrated in FIGS. 10 and 11, the variflex technology is used in an endoscopic transgastric surgery where one or more steerable working channels 50 having the variable flexibility of the present invention are attached to an endoscope 60 or over the endoscope 60 as an overtube (not illustrated). Such a channel 50 is used to steer devices 70 such as snares, biopsy forceps, graspers, injection needles, etc. The channel embodiment of FIGS. 10 and 11 has a variflex distal portion 52 and a non-variflex proximal portion 54. Of course, any portion of the channel 50 can be variflex or not. A stylette 70 with a flexible pre-formed section at its distal tip is inserted into the working channel 50 with the variflex section 52 in the soft, flexible state so that the variflex section 52 takes the shape of stylette 70. The variflex section 52, then, is stiffened. Devices are, then, able to be inserted into the working channel and through the bent variflex section 52.

The variflex invention of the instant application can also be applied to spinal procedures. For example, spinal fixation rods are used to immobilize and stabilize segments of the thoracic, lumbar, and sacral spine. Certain acute and chronic spinal disorders may make it necessary to surgically stabilize the spine using rods and screws. Disorders that cause spinal instability or deformity include degenerative spondylolisthesis, fractures, scoliosis, kyphosis, spinal tumor, and failed previous fusion (pseudoarthrosis). The variflex technology of the present invention is used with these systems to make adjustments to the patient's posture after they are implanted. The rods and screws can contain a section or sections of the variflex technology. The variflex sections are softened to allow for adjustment of the patient's posture. Once the patient's posture is adjusted to the desired position, the variflex section(s) is/are hardened to maintain the desired posture.

The variflex invention of the instant application can also be applied to extremity immobilization devices. For example, splints, casts, or neckbraces made from sheets of variflex material could be heated (whether with implanted heaters or external heaters such as heat packs) to make the material pliable to be custom fitted to the patient. After removing the heat, the device hardens to provide support to the body part. Such configurations are especially desirable in emergency situations where speed is important, as hardening of the variflex material is extremely fast.

The variflex invention of the instant application can also be applied to endovascular application. For example, when such a catheter or device is used in a contralateral approach during diagnostic and interventional procedures, the catheter or device is inserted in its flexible state and is positioned around the bifurcation of the aorta. After the catheter or device has been placed in the opposite arm of the bifurcation, it can be stiffened in place to stabilize the catheter or device and allow the user to advance other devices through or around the device that has the variflex technology incorporated into one or more segments along its length.

The variflex invention of the instant application can also be applied to guiding catheters, stent delivery systems, balloon catheters, and steerable wires as set forth in the cardiovascular applications above. The invention can also be used with neuroradiology procedures. For example, in a thrombectomy, devices used to remove blood clots can be made to perform better by the application of the variflex technology. Specifically, such variable stiffness devices can be incorporated into a small straight flexible catheter that can be changed into a corkscrew configuration at the tip by insertion of a stylette having the desired shape and, then, stiffening the tip of the catheter to assume the same configuration of the stylette.

The variflex invention of the instant application can also be applied to coil delivery systems. Incorporation of the variflex technology of the present invention into a coil delivery system allows the device to be inserted in its flexible state to a distal location within the vasculature and to be subsequently stiffened to stabilize the delivery system in the blood vessel to be treated and to facilitate the deployment of the coil into the target vessel.

The variflex invention of the instant application can also be applied in the oncology field. Indwelling venous catheters used for administration of different chemotherapeuting agents can be stabilized in place after insertion using the variflex technology of the present invention. Specifically, it can be used to stiffen the catheter wall and cause the catheter to assume the shape of the anatomy in which it is placed. When it is time to remove the catheter, it can be made flexible for easy withdrawal from the vasculature.

The variflex invention of the instant application can also be applied in the urology field. For example, Foley catheters can be made more stable and prevent migration by using the variflex technology at the distal tip. The Foley catheter containing a variflex section on the distal end is inserted into the urethra with the variflex section in the soft, flexible condition. Once the variflex section is in the bladder, a preformed stylette (possibly a pigtail) is inserted into the Foley catheter. The variflex section is, then, hardened to maintain the shape of the stylette and, therefore, will not migrate. Insertion of a stylette with the desired shape, followed by a stiffening of the catheter, changes the tip of the catheter to a "pigtail" configuration to stabilize the catheter inside the bladder, thus obviating the need for a balloon. It is noted that a straight, flexible Foley catheter is easier to insert than the standard curved catheters. Additionally, devices used to treat benign Protatic Hyperplasia can be easier to insert and deliver to the prostate by the use of the Variflex technology. Insertion of any device in flexible form followed by subsequent stiffening facilitates reaching the prostate for treatment using dilatation or resection devices.

Exemplary non-medical uses of the variflex technology of the present invention include clothes, shoes, boots, and other wearable items that could conform to a user's body and, thereafter, be locked in place. The variflex technology could be used for body armor that is pliable when the person is not in imminent danger. In such a flexible state, the armor would be comfortable for the user. When the user enters a precarious situation, the armor is activated to harden for the desired level of protection.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A controllable stiffness catheter, comprising:
   a shaft comprising:
   a handle;
   an inner sheath having a proximal end connected to the handle, a distal end and defining an access lumen;
   an outer sheath surrounding the inner sheath to the distal end and defining an annulus therebetween, the annulus comprising a proximal portion connected to the handle and having a vacuum connection at which a vacuum is applied to the annulus;
   a mechanical stiffener disposed at least at a longitudinal portion of the annulus, the inner and outer sheaths and the mechanical stiffener being sized to have at least the longitudinal portion sized for neurological vascular procedures, the outer sheath having a substantially constant outer diameter over the longitudinal portion of the annulus to the distal end, the inner and outer sheaths being longitudinally fixed with respect to one another; and
   a vacuum device fluidically connected to the vacuum connection and configured to apply the vacuum to the annulus and, responsive to the vacuum being applied to the vacuum connection:
   pressure is lowered within the annulus;
   the outer sheath contacts the mechanical stiffener; and
   the shaft is stiffened at least at the longitudinal portion at which the mechanical stiffener is disposed to substantially and passively maintain a current shape of the shaft at least at the longitudinal portion.

2. The catheter according to claim 1, wherein, responsive to the vacuum being applied to the annulus through the vacuum connection, the longitudinal portion substantially maintains the current shape and a current orientation of the shaft at least at the longitudinal portion.

3. The catheter according to claim 1, wherein, responsive to the longitudinal portion being disposed within neurological vasculature and the vacuum being applied to the annulus through the vacuum connection, the shaft is stiffened at least at the longitudinal portion at which the mechanical stiffener is disposed to substantially maintain the current shape and a current orientation of the shaft in the neurological vasculature.

4. The catheter according to claim 1, wherein the mechanical stiffener allows fluid between the inner sheath and the outer sheath to move about the mechanical stiffener.

5. The catheter according to claim 1, wherein the mechanical stiffener is disposed outside the inner sheath.

6. The catheter according to claim 1, wherein the mechanical stiffener is disposed inside the outer sheath.

7. The catheter according to claim 1, wherein, responsive to the vacuum being applied to the annulus through the vacuum connection, the shaft is stiffened at least at the longitudinal portion at which the mechanical stiffener is disposed without substantially straightening the shaft at the longitudinal portion.

8. The catheter according to claim 1, wherein a magnitude of a pressure difference between an outside of the catheter and the interior of the annulus affects stiffness of the shaft such that, as the pressure difference increases, the stiffness at least at the longitudinal portion increases.

9. The catheter according to claim 1, wherein the outer sheath comprises polyurethane and the inner sheath comprises PTFE.

10. The catheter according to claim 1, wherein an entire length of the shaft is controllable in stiffness.

11. The catheter according to claim 1, wherein the longitudinal portion is a distal 20 cm of the shaft.

12. The catheter according to claim 1, wherein the mechanical stiffener is subdivided into different stiffening segments.

13. The catheter according to claim 1, wherein the shaft has a proximal portion and the shaft further comprises a titer fitting at the proximal portion.

14. The catheter according to claim 13, wherein:
   the luer fitting provides access to the access lumen; and/or
   the luer fitting fluidically connects to the vacuum connection and is configured to removably fluidically connect to the vacuum device; and/or
   the luer fitting comprises first and second luer fittings, the first luer fitting providing access to the access lumen and the second luer fitting fluidically connecting to the vacuum connection and configured to removably fluidically connect to the vacuum device.

15. The catheter according to claim 1, wherein:
   the access lumen has a diameter of at least 0.4064 mm; and
   the shaft has an outer diameter no greater than 1.651 mm.

16. The catheter according to claim 1, wherein:
   the outer sheath comprises a smooth inner surface; and
   the mechanical stiffener is movable within the annulus with respect to the smooth inner surface of the outer sheath.

17. The catheter according to claim 1, wherein the mechanical stiffener is at least one of granular aluminum oxide and granular silica.

18. The catheter according to claim 17, wherein, responsive to the vacuum being applied to the annulus through the vacuum connection, the outer sheath compresses grains of the mechanical stiffener to stiffen the shaft at least at the portion at which the mechanical stiffener is disposed without straightening the shaft at the portion.

19. The catheter according to claim 1, wherein;
   the inner sheath has an outside surface;
   the outer sheath has an inside surface; and
   the mechanical stiffener comprises a surface roughening on at least one of the outside surface of the inner sheath and the inside surface of the outer sheath.

20. A controllable stiffness catheter, comprising:
   a shaft comprising:
   a handle
   an inner sheath having a proximal end connected to the handle and a distal end and defining an access lumen;
   an outer sheath surrounding the inner sheath to the distal end and defining an annulus therebetween, the annulus comprising a proximal portion connected to the handle and having a vacuum connection at which a vacuum is applied to the annulus;
   a mechanical stiffener disposed at least at a longitudinal portion of the annulus, the inner and outer sheaths and the mechanical stiffener being sized to have at least the longitudinal portion sized for neurological vascular procedures, the outer sheath having a substantially constant outer diameter over the longitudinal portion of the annulus to the distal end, the inner and outer sheaths being longitudinally fixed with respect to one another; and
   a vacuum device fluidically connected to the vacuum connection and configured to apply the vacuum to the annulus and, responsive to the vacuum being applied to the vacuum connection:
   pressure is lowered within the annulus;
   the outer sheath contacts the mechanical stiffener; and the shaft is stiffened at least at the longitudinal portion at which the mechanical stiffener is disposed without substantially straightening the shaft at the longitudinal portion.

* * * * *